United States Patent [19]

Mitchell

[11] Plant 4,929

[45] Nov. 9, 1982

[54] AZALEA PLANT NAMED SOUTHERN BELLE

[76] Inventor: Luther L. Mitchell, P.O. Box 3366, Oxford, Ala. 36203

[21] Appl. No.: 216,313

[22] Filed: Dec. 15, 1980

[51] Int. Cl.[3] ..... A01H 5/00

[52] U.S. Cl. ..... Plt./56

[58] Field of Search ..... Plt./56

*Primary Examiner*—Robert E. Bagwill

[57] ABSTRACT

An azalea plant characterized by its variegated foliage and pink, hose-in-hose blossoms.

1 Drawing Figure

My invention relates to a new and distinct cultivar of the Rutherford azalea plant, originating as a chance mutation from Allan 72 in my nursery in Oxford, Ala.

My new cultivar was first observed in 1965 and was selected for its new and distinct variegated foliage.

Asexual propagation by cuttings of this new plant as performed in my nursery at Oxford, Ala., shows that this plant reproduces true to form with the above characteristics transmitted through succeeding propagations.

References to color in the following description refer to the Horticulture Colour Charts issued by the Royal Horticultural Society. Where there are other references to color, the ordinary dictionary meanings of the terms are intended.

DESCRIPTION OF THE DRAWINGS

The accompanying illustrations show in natural color, this pink, hose-in-hose azalea with variegated foliage as fairly as can possibly be obtained by this method of illustration.

THE PLANT

Foliage:

*Leaves.*—Alternate, evergreen lanceolate to oblanceolate, 2½ to 3 inches (6.3 cm to 7.7 cm) long, ⅜ to 14/16 inch (1.0 cm to 2.4 cm) wide, leaves often wider beyond the middle; leaf margin entire, often with a wavy or uneven edge.

Color: Mature green leaves are 147B, Fan 3, new leaves in spring have a soft, light grey-green color. The leaf is distinct, due to a narrow-variegated margin, 1/32 to 1/16 inch (0.08 cm to 0.16 cm) in width, the yellow-white leaf margin in the 158B, Fan 4, (yellow-white group).

Growth habit: Medium to medium-large to six feet or more at maturity, plants are very floriferous.

Branches: Mature, one-year stems are brown, covered with appressed, minute, light tan to white hairs.

Hardiness: Hardy without protection in Zone 7 and Zone 8, as shown in the Plant Hardiness Zone Map, Misc. Publication #814, Agricultural Research Service, U.S.D.A., additional hardiness to be determined in the future. As to hardiness, there has been no winter damage or seasonal damage to plants of this new cultivar in my nursery during the last three years. Plants have been exposed to six degrees F. in March, 1980, with no damage noted.

FLOWERS

Hose-in-hose, pink (62a, Fan 2), with slightly darker spots in upper petal. Flowers are 1½ to 2¼ inches across, width of petals (0.39 cm to 0.58 cm). Flowers are typical of azalea (Allen 72).

COMPARISON

This new cultivar differs from the following variegated foliaged azaleas as follows:

'Variegated Giant Ruffles' (Florida) (unpatented) has large, single pink flowers.

'Purple Taber' (California) (unpatented) has single, light purple flowers and mature stems are light tan in color.

*Rhododendron indicum* 'Shirafugi' NA 40802 and *Rhododendron satsuki* 'Shirafugi' NA 41026 (probably one and the same) has small leaves, less than 1½ inch long and single white to white-to-pink margins on flowers.

*Rhododendron simsi* variegated 45,628 (University of California Arboretum) has single pink flowers.

I claim:

1. A new and distinct cultivar of the Rutherford azalea, with features herein shown and described, characterized by the distinct narrow, yellow-white margins.

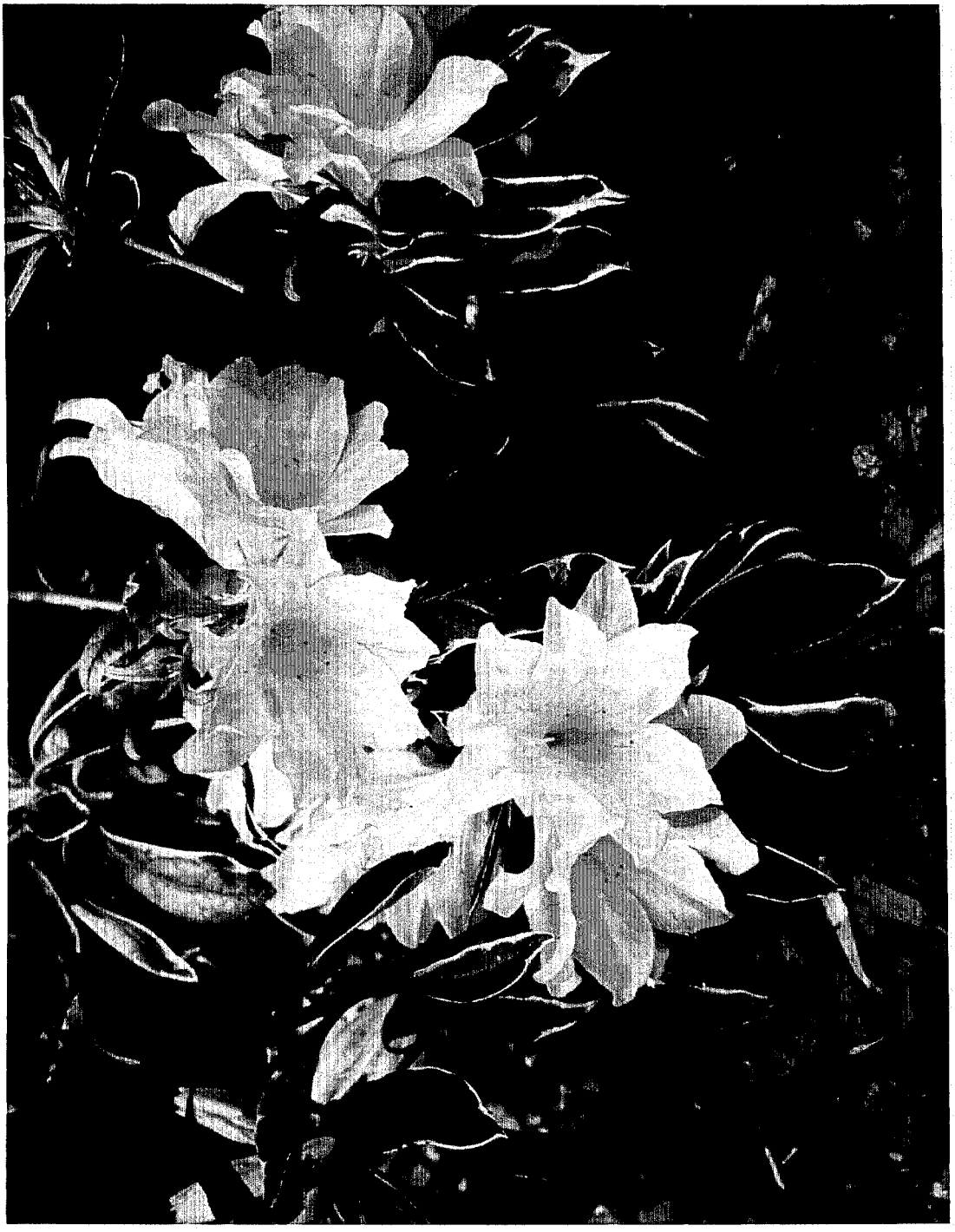

* * * * *